United States Patent
Ternes et al.

(10) Patent No.: US 10,549,106 B2
(45) Date of Patent: Feb. 4, 2020

(54) EXTERNAL AUDIT OF IMPLANTABLE MEDICAL DEVICE

(71) Applicant: Cardiac Pacemakers, Inc., St. Paul, MN (US)

(72) Inventors: David J. Ternes, Roseville, MN (US); Pramodsingh Hirasingh Thakur, Woodbury, MN (US); Stephen B. Ruble, Lino Lakes, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 31 days.

(21) Appl. No.: 15/675,427

(22) Filed: Aug. 11, 2017

(65) Prior Publication Data

US 2018/0078778 A1    Mar. 22, 2018

Related U.S. Application Data

(60) Provisional application No. 62/373,463, filed on Aug. 11, 2016.

(51) Int. Cl.
*A61N 1/372*      (2006.01)
*A61N 1/37*       (2006.01)
(Continued)

(52) U.S. Cl.
CPC .......... *A61N 1/37282* (2013.01); *A61N 1/37* (2013.01); *A61N 1/37254* (2017.08); *A61N 1/36521* (2013.01); *A61N 1/375* (2013.01)

(58) Field of Classification Search
CPC .. A61N 1/37282; A61N 1/37; A61N 1/37254; A61N 1/37252; A61N 1/37247;
(Continued)

(56) References Cited

U.S. PATENT DOCUMENTS

| 8,301,241 B2 | 10/2012 | Ternes et al. |
| 2015/0157260 A1* | 6/2015 | Zhang .................. A61B 5/7275 600/323 |
| 2017/0296086 A1 | 10/2017 | Ternes et al. |

OTHER PUBLICATIONS

Hayes, David, et al., "Cardiac resynchronization therapy and the relationship of percent biventricular pacing to symptoms and survival", Heart Rhythm, vol. 8, No. 9, (Sep. 2011), 1469-1475.

(Continued)

*Primary Examiner* — Catherine M Voorhees
*Assistant Examiner* — Roland Dinga
(74) *Attorney, Agent, or Firm* — Schwegman Lundberg & Woessner, P.A.

(57) ABSTRACT

Systems and methods for auditing an operation of an ambulatory medical device (AMD) are described. A system may include an auditor device and an analyzer circuit communicatively coupled to each other. The auditor device can sense from the patient, independently of and during the operation of the AMD, information about the operation of the AMD including sensed electrostimulation and a physiological signal in response to the electrostimulation. The analyzer unit may generate a device audit indicator indicating the functionality and performance of the AMD using the sensed physiological signal and the sensed AMD operation information. The system may output the device audit indicator to a user or a process, or to program device therapy for the AMD based on the device audit indicator.

20 Claims, 4 Drawing Sheets

(51) Int. Cl.
*A61N 1/375* (2006.01)
*A61N 1/365* (2006.01)

(58) Field of Classification Search
CPC .. A61N 1/3627; A61N 1/375; A61N 1/36521; A61B 5/686; A61B 5/6869; A61B 5/4836; A61B 5/0816; A61B 5/053; A61B 5/042; A61B 5/02405; A61B 5/024; A61B 5/0215; A61B 5/01; A61B 5/091
See application file for complete search history.

(56) References Cited

OTHER PUBLICATIONS

Lo, Monica Y., et al., "Maximizing Cardiac Resynchronization Therapy in Patients With Atrial Fibrillation", The Journal of Innovations in Cardiac Rhythm Management, 2 (Dec. 2011), 584-593.
Mullens, Wilfried, et al., "Insights From a Cardiac Resynchronization Optimization Clinic as Part of a Heart Failure Disease Management Program", Journal of the American College of Cardiology, vol. 53, No. 9, (2009), 765-773.
Thakur, Pramodsingh H., et al., "Syncing Multiple Sources of Physiological Data, U.S. Appl. No. 62/276,686, filed Jan. 8, 2016".

* cited by examiner

US 10,549,106 B2

EXTERNAL AUDIT OF IMPLANTABLE MEDICAL DEVICE

CLAIM OF PRIORITY

This application claims the benefit of priority under 35 U.S.C. § 119(e) of U.S. Provisional Patent Application Ser. No. 62/373,463, filed on Aug. 11, 2016, which is herein incorporated by reference in its entirety.

TECHNICAL FIELD

This document relates generally to medical devices, and more particularly, to systems and methods for automatic audit of a medical device.

BACKGROUND

Congestive heart failure (CHF) is a leading cause of death in the United States, and is the major cause of hospitalization in patients 65 years and older. CHF is also the single largest Medicare expenditure; accounting for approximately $4 billion annually. CHF occurs when the heart is unable to adequately supply enough blood to maintain a healthy physiological state. CHF may be treated by drug therapy, or by an ambulatory medical device (AMD) such as an implantable medical device (IMD).

Some IMDs may chronically stimulate excitable tissues or organs, such as a heart, to help restore or improve cardiac performance in a patient with CHF, or to treat abnormal cardiac rhythms. Such IMDs may have electrodes that may be positioned within the heart or on a surface of the heart. The electrodes may be electrically coupled to an electronics unit such as a pulse generator, such as via a lead, and may be used to deliver electrostimulation to the heart. One type of electrostimulation is cardiac resynchronization therapy (CRT) achieved by simultaneous or synchronized pacing of both left and right ventricles, which has been shown to be effective in improving cardiac function in some CHF patients with a depressed ejection fraction and dyssynchrony of inter- or intraventricular electromechanical activation.

SUMMARY

Cardiac electrostimulation such as CRT may rectify dyssynchrony and improve cardiac function in some CHF patients. However, in some other patients with advanced CHF, CRT may not exhibit a positive response to CRT therapy. Even in some patients who demonstrate positive responses to CRT, the long-term therapy efficacy and patient outcome may not be optimal such as due to heart failure progression and development of one or more comorbidities. For example, atrial fibrillation (AF) is the most common arrhythmia in patients with CHF. Presence of AF may worsen the CHF, and may also completely or partially preclude biventricular pacing treatment, thus imposes significant negative impact on CRT response. In addition to arrhythmias or other comorbidities, persistent mechanical dyssynchrony, anemia, suboptimal medical therapy, or lack of compliance may also contribute to non-response or suboptimal response to CRT therapy. Other factors associated with the function of the IMD and programming of the CRT may also have an impact on patient response to CRT, such as device and lead integrity, electrode positioning, selection of pacing vectors, programming of stimulation intensity, or programming of timing offset between stimulations at various cardiac sites, among others.

Timely assessment of the operation and functionality of the IMD may help in titrating CRT therapy for individual patient and therefore enhance the CRT response. For example, response to CRT may be characterized by how frequent the biventricular pacing is delivered, and how frequent the delivered stimulation may capture the viable tissue by eliciting a propagatable cardiac depolarization. Effective monitoring of the delivery of the electrostimulation and the evoked physiological response may provide useful information for tailoring the CRT therapy to meet patient needs. Some IMDs are able to sense the delivery of electrostimulation and the resultant tissue response. However, information as acquired by the IMD, such as presence, count, or other statistics of pacing pulses, the evoked tissue responses, or the therapeutic effect of the CRT may not always be accurate, such as due to interference, noises, or other physiological or non-physiological confounding factors. The present inventors have recognized a need of systems and methods that may independently monitor the operation of an IMD to detect electrostimulation delivery and patient response, and tailor the device therapy to improve positive CRT response.

This document discusses, among other things, a system for auditing an operation of an AMD. The system may include an auditor device that senses, independently of and during the operation of the AMD, information about AMD operation including sensed electrostimulation and a physiological signal in response to the electrostimulation. The system may generate a device audit indicator indicating the functionality and performance of the AMD using the sensed physiological signal and the sensed AMD operation information. The device audit indicator may be presented to a user, or be used in programming device therapy for the AMD. Although the discussion herein focuses on cardiac stimulation such as CRT, this is meant only by way of example and not limitation. The systems, devices, and methods discussed in this document may also be used for monitoring the operation of an AMD that delivers electrostimulation to other targets such as neural tissues.

Example 1 is a system for automatically auditing an operation of an ambulatory medical device (AMD) associated with a patient. The system may comprise: an auditor device and an analyzer unit communicatively coupled to the auditor device. The auditor device may be configured to sense from the patient, independently of and during the operation of the AMD, a physiological signal and information about AMD operation. The analyzer unit may be configured to receive from the auditor device the sensed physiological signal and the sensed AMD operation information, generate a device audit indicator indicating a performance of the AMD using the sensed physiological signal and the sensed AMD operation information, and output the device audit indicator to a user or a process.

In Example 2, the subject matter of Example 1 optionally includes the AMD communicatively coupled to the analyzer unit. The AMD may be configured to generate information about the operation of AMD. The analyzer unit may receive the AMD operation information generated by the AMD, and generate the device audit indicator further using the AMD operation information generated by the AMD.

In Example 3, the subject matter of Example 2 optionally includes the analyzer unit that may further include a programmer circuit configured to program the AMD based on the device audit indicator.

In Example 4, the subject matter of any one or more of Examples 2-3 may optionally include the AMD that includes a therapy circuit to deliver a therapy to the patient. The programmer circuit of the analyzer unit may be configured to program the AMD including program a therapy with specified therapy parameters.

In Example 5, the subject matter of any one or more of Examples 1-4 optionally include the auditor device that includes an ambulatory device associated with the patient. The ambulatory device may include one of: an ambulatory sensor patch; a wearable device; or a portable external monitor. The ambulatory device may include an implantable or subcutaneous monitor. The ambulatory device may include one or more of a group including: an ambulatory sensor patch; a wearable device; a portable external monitor; or an implantable or subcutaneous monitor. In an example, one or more of the ambulatory sensor patch, the wearable device, the portable external monitor, or the implantable or subcutaneous monitor may be removed from the group.

In Example 6, the subject matter of any one or more of Examples 1-5 optionally include the auditor device that includes an immobile device configured to sense the patient physiological signal in an ambient environment of the patient.

In Example 7, the subject matter of any one or more of Examples 1-6 optionally include the AMD operation information sensed by the auditor device that may include a sensed electrostimulation delivered via the AMD. The sensed physiological signal may include a sensed physiological response to the electrostimulation. The device audit indicator may indicate an effectiveness of the electrostimulation based on the sensed electrostimulation and the sensed physiological response to the electrostimulation.

In Example 8, the subject matter of Example 7 optionally includes the AMD for delivering electrostimulation including a cardiac stimulation or a neural stimulation delivered via the AMD.

In Example 9, the subject matter of any one or more of Examples 7-8 optionally include the analyzer unit that may be configured to generate the device audit indicator indicating a therapeutic effect or an undesirable side effect of the electrostimulation.

In Example 10, the subject matter of Example 9 optionally includes the therapeutic effect that may include one or more statistics of tissue capture, non-capture, or fusion in response to the electrostimulation.

In Example 11, the subject matter of Example 10 optionally includes the undesirable side effect that may include one or more of unwanted phrenic nerve stimulation or unwanted laryngeal stimulation.

In Example 12, the subject matter of any one or more of Examples 1-11 optionally include the analyzer unit that may be configured to generate the device audit indicator including device diagnostic information about the AMD.

In Example 13, the subject matter of any one or more of Examples 1-12 optionally include the analyzer unit that may be configured to generate the device audit indicator including a recommendation for programming the AMD.

In Example 14, the subject matter of any one or more of Examples 1-13 optionally include first and second auditor devices each communicatively coupled to the analyzer unit. The first auditor device may be configured to sense, independently of and during the operation of the AMD, a first physiological signal and first AMD operation information. The second auditor device may be configured to sense, independently of and during the operation of the AMD, a different second physiological signal and second AMD operation information. The analyzer unit may be configured to generate the device audit indicator using the first and second sensed AMD operation information.

In Example 15, the subject matter of Example 14 optionally includes the first auditor device that may be configured to sense the first physiological signal at a first body location, and the second auditor device that may be configured to sense the second physiological signal at a different second body location.

In Example 16, the subject matter of any one or more of Examples 1-15 optionally include the AMD communicatively coupled to the auditor device, wherein at least a portion of the analyzer unit is incorporated within the auditor device.

Example 17 is a method of operating an auditor device to automatically audit an operation of an ambulatory medical device (AMD) associated with a patient. The method may comprise steps of: sensing from the patient, via the auditor device and independently of and during the operation of the AMD, a physiological signal and information about AMD operation; generating a device audit indicator indicating a performance of the AMD using the sensed physiological signal and the sensed AMD operation information; and outputting the device audit indicator to a user or a process.

In Example 18, the subject matter of Example 17 optionally includes establishing a communication link between the auditor device and an analyzer unit, and transmitting the sensed physiological signal and the sensed AMD operation information to the analyzer unit via the communication link.

In Example 19, the subject matter of Example 17 optionally include generating, via the AMD, information about the operation of AMD, wherein generating the device audit indicator includes further using the information about the operation of AMD generated by the AMD.

In Example 20, the subject matter of Example 17 optionally includes programming the AMD that may include programming a therapy based on the device audit indicator.

In Example 21, the subject matter of Example 17 optionally includes the AMD operation information sensed by the auditor device that may include a sensed electrostimulation delivered via the AMD. The sensed physiological signal may include a sensed physiological response to the electrostimulation. The device audit indicator may indicate an effectiveness of the electrostimulation based on the sensed electrostimulation and the sensed physiological response to the electrostimulation.

In Example 22, the subject matter of Example 21 optionally includes the electrostimulation delivered via the AMD including a cardiac stimulation or a neural stimulation.

In Example 23, the subject matter of Example 21 optionally include generating the device audit indicator including generating one or more indicators of: statistics of tissue capture, non-capture, or fusion in response to the electrostimulation; stimulation site recognition; a therapeutic effect of the electrostimulation; an undesirable side effect of the electrostimulation; device diagnostic information about the AMD; or a recommendation for programming the AMD.

This Summary is an overview of some of the teachings of the present application and not intended to be an exclusive or exhaustive treatment of the present subject matter. Further details about the present subject matter are found in the detailed description and appended claims. Other aspects of the invention will be apparent to persons skilled in the art upon reading and understanding the following detailed description and viewing the drawings that form a part thereof, each of which are not to be taken in a limiting sense. The scope of the present invention is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

DETAILED DESCRIPTION

Disclosed herein are systems, devices, and methods for auditing an operation of an ambulatory medical device (AMD). The system may include an auditor device that may generate, independently of and during the operation of the AMD, information about AMD operation including sensed electrostimulation, and sense a physiological signal in response to the electrostimulation. The system may generate a device audit indicator indicating the functionality and performance of the AMD using the sensed physiological signal and the sensed AMD operation information.

Figure 1:
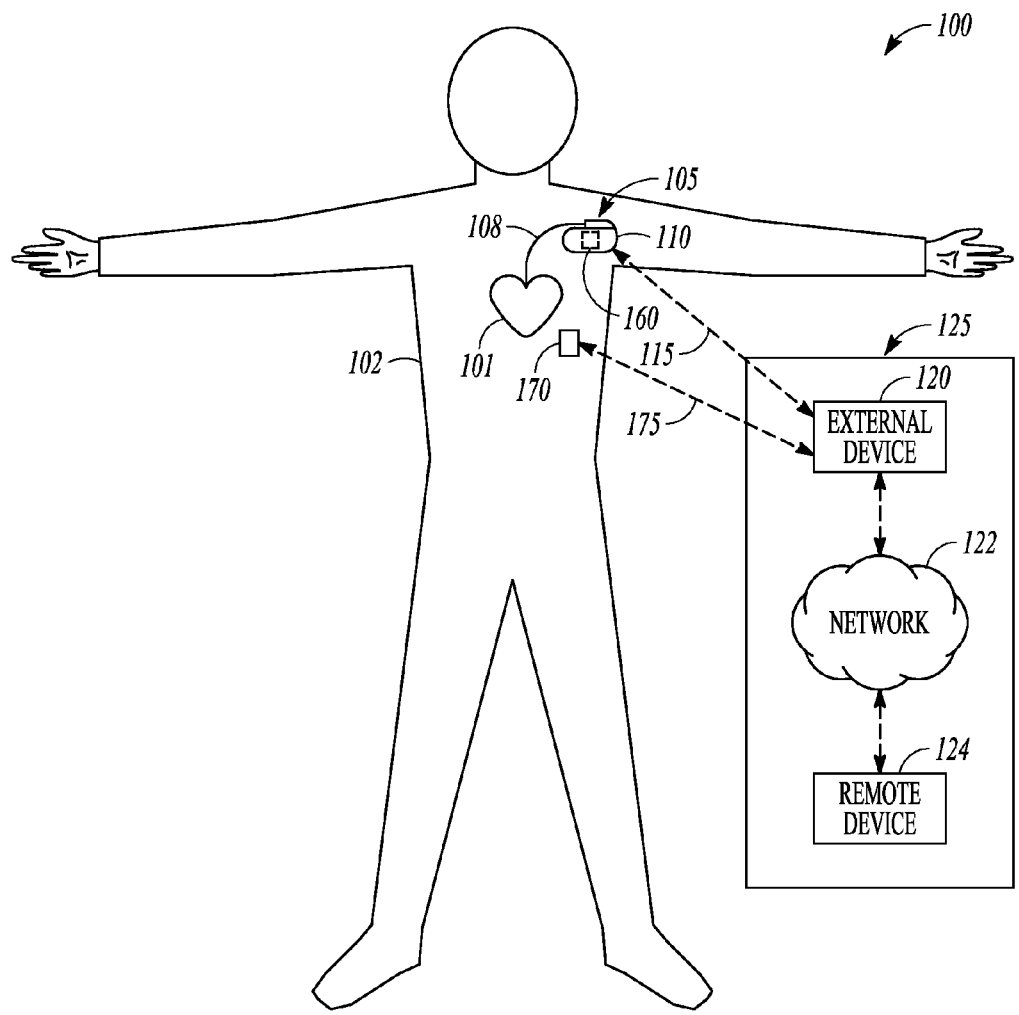
FIG. 1 illustrates generally an example of a patient management system and portions of an environment in which the patient management system may operate.

FIG. 1 illustrates generally an example of a patient management system 100 and portions of an environment in which the patient management system 100 may operate. The patient management system 100 may be used to audit the operation of an ambulatory medical device for monitoring the progression of a chronic disease such as heart failure, and providing therapies such as cardiac electrostimulation. The patient management system 100 may include an auditor device 170 associated with the patient body 102, an external system 125, and a communication link 175 that provides communication between the auditor device 170 and the external system 125. The patient management system 100 may additionally include an ambulatory system 105 which includes an ambulatory medical device (AMD) 110. The external system 125 and the auditor device 170 may collaboratively audit the operation of the AMD 110.

The AMD 110 may include an implantable device that may be implanted within the body 102. The AMD 110 may be coupled to a heart 101 via a lead system 108 to deliver a therapy to a target site such as in the heart 101. In some examples, the AMD 110 may be wirelessly coupled to electrodes positioned at the target site for delivering a therapy. Examples of the implantable device may include, but are not limited to, pacemakers, pacemaker/defibrillators, cardiac resynchronization therapy (CRT) devices, cardiac remodeling control therapy devices, neuromodulators, drug delivery devices, biological therapy devices, diagnostic devices such as cardiac monitors or loop recorders, or patient monitors, among others. The AMD 110 may alternatively or additionally include subcutaneously implanted devices such as a subcutaneous ICD or a subcutaneous diagnostic device, wearable medical devices, or other external monitoring or therapeutic medical devices such as a bedside monitor.

The lead system 108 may include one or more transvenously, subcutaneously, or non-invasively placed leads or catheters. Each lead or catheter may include one or more electrodes. The arrangements and uses of the lead system 108 and the associated electrodes may be determined based on the patient need and the capability of the AMD 110. The lead system 108 and the associated electrodes may deliver therapy to treat cardiac or pulmonary diseases. The therapies may include pacing, cardioversion, defibrillation, neuromodulation, drug therapies, or biological therapies, among other types of therapies. In an example, the therapies may include cardiac resynchronization therapy (CRT) for rectifying dyssynchrony and improving cardiac function in CHF patients. The electrodes on the lead system 108 may be positioned inside or on a surface of at least a portion of the heart, such as a right atrium (RA), a right ventricle (RV), a left atrium (LA), or a left ventricle (LV). In an example, the lead system 108 and the associated electrodes may be implanted subcutaneously. The associated electrodes on the lead system 108 may be positioned at the patient's thorax or abdomen to sense intrinsic physiological signals indicative of cardiac or pulmonary activities, or physiological responses to diagnostic or therapeutic stimulations to a target tissue.

The AMD 110 may include a monitor 160 for sensing a physiological signal, such as by using a physiological sensor or the electrodes associated with the lead system 108. Examples of the physiological signal may include one or more of electrocardiogram, intracardiac electrogram, arrhythmia, heart rate, heart rate variability, intrathoracic impedance, intracardiac impedance, arterial pressure, pulmonary artery pressure, left atrial pressure, RV pressure, LV coronary pressure, coronary blood temperature, blood oxygen saturation, one or more heart sounds, intracardiac acceleration, physical activity or exertion level, physiological response to activity, posture, respiration rate, tidal volume, respiratory sounds, body weight, or body temperature. The AMD 110 may initiate or adjust therapies based on the sensed physiological signals.

The auditor device 170 may include an ambulatory device, such as an ambulatory sensor patch, a wearable device, a portable external device, or an implantable or subcutaneous monitor. The auditor device 170 may additionally or alternatively include an immobile device that does not move along or in direct contact with the patient, but instead may be positioned in an ambient environment of the patient, such as attached to a seat, under a pillow, under a mattress, at the bedside, or inside the car, among other ambient locations. Such an immobile auditor device may sense a patient posture, activity, or other physical or physiological signal when the patient enters or remains within the ambient environment of the auditor device.

The auditor device 170 may sense a physiological signal independently of and during the operation of the AMD 110. The physiological signals sensed by the sensors may provide information about the patient's physiological response during the operation of the AMD 110. The auditor device 170 may also sense the operation of the AMD 110, such as measurements when the AMD 110 executes a self-diagnostic test (e.g., lead integrity test via lead impedance measurement, battery status check), sensing of a physiological signal (e.g., evoked cardiac electrogram, tissue impedance, heart sounds, blood pressure signal), a medical diagnostic decision (e.g., worsening of heart failure, respiratory disease, or renal failure), or a therapy delivery, among others. In an example, the information about operation of the AMD 110 that is sensed by the auditor device 170 may include a sensed electrostimulation delivered via the AMD 110 in the perspective of the auditor device 170, and the physiological signal may include a physiological response to the electrostimulation. The auditor device 170 may transmit the sensed electrostimulation and the sensed physiological signal to the external system 125 for producing an audit of the operation of the AMD 110.

The external system 125 may include an external device 120 in proximity of the AMD 110, a remote device 124 in a location relatively distant from the AMD 110, and a telecommunication network 122 linking the external device 120 and the remote device 124. The external system 125 may be used to program the auditor device 170 via the communication link 175. The communication link 175 may include wired or wireless connections. Examples of the wireless connection may include radiofrequency signals, inductive coupling, capacitive coupling, optical signals, acoustic signals, conducted communication signals, or any other signals suitable for communication. In an example, the external system 125 may include a local programmer. In another example, the external system 125 may include a patient management system for remote access of the auditor device 170. Via the communication link 175, the sensed physiological signal and the sensed information about the operation of the AMD 110, such as produced by the auditor device 170, may be transmitted to the external system 125, which may generate a device audit indicator indicating the operation, functionality, or effectiveness of therapies of the AMD 110.

The external system 125 may also program the ambulatory system 105 via a telemetry link 115. The telemetry link 115 may be an inductive telemetry link, a capacitive telemetry link, or a radio-frequency telemetry link. The telemetry link 115 may provide for data transmission from the AMD 110 to the external system 125. This may include, for example, transmitting real-time physiological data acquired by the AMD 110, extracting physiological data acquired by and stored in the AMD 110, extracting patient history data such as data indicative of occurrences of arrhythmias, occurrences of decompensation, and therapy deliveries recorded in the AMD 110, and extracting data indicating an operational status of the AMD 110 (e.g., battery status and lead impedance). The telemetry link 115 may also provide for data transmission from the external system 125 to the AMD 110. This may include, for example, programming the AMD 110 to perform one or more functions including acquiring physiological data, performing self-diagnostic test, analyzing the physiological data, or delivering a therapy, among others. In some examples, the external system 125 may program the AMD 110 based on the device audit indicator.

Portions of the auditor device 170, the AMD 110, or the external system 125 may be implemented using hardware, software, a combination of hardware and software, such as an application-specific circuit constructed or configured to perform one or more particular functions, or a general-purpose circuit programmed or otherwise configured to perform one or more particular functions. Such a general-purpose circuit may include a microprocessor or a portion thereof, a microcontroller or a portion thereof, or a programmable logic circuit, or a portion thereof. For example, a "comparator" may include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2A:
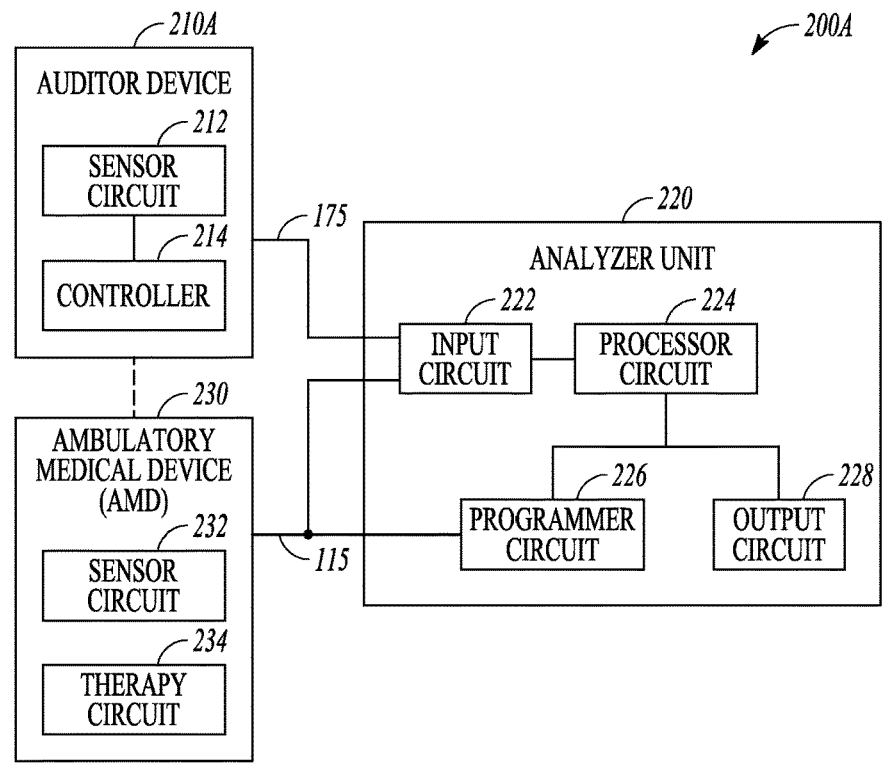
FIGS. 2A-B illustrate generally examples of device audit systems for automatic auditing functionality of and effectiveness of therapy delivery in a medical device.
Figure 2B:
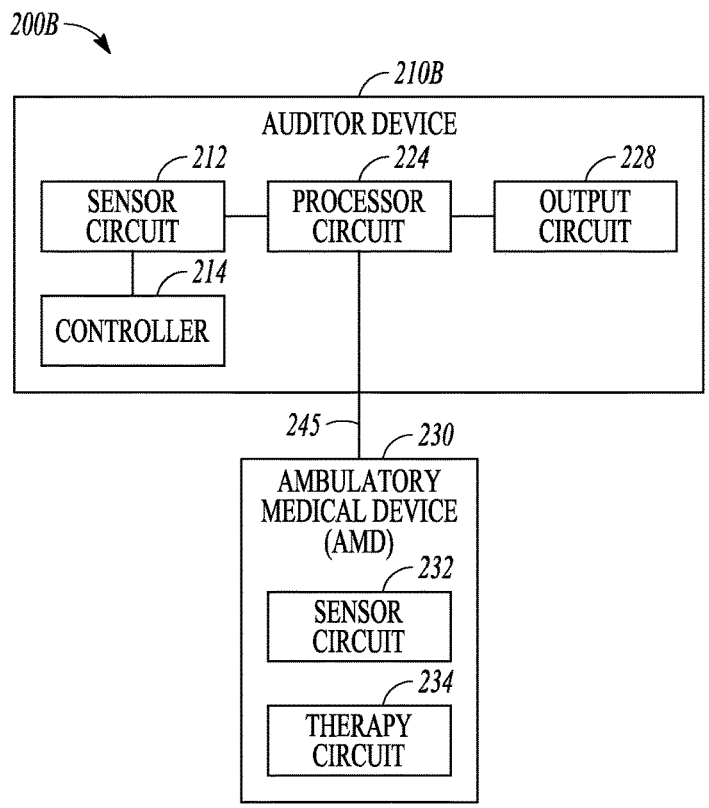

FIGS. 2A-B illustrate generally examples of device audit systems 200A and 200B for automatic auditing the functionality of a medical device such as the AMD 110 in FIG. 1 and the effectiveness of a therapy delivery thereof. The device audit system 200A in FIG. 2A may also be used to automatically program the medical device based on the audit of the device functionality and therapy delivery. In FIG. 2A, the device audit system 200A may be distributedly implemented among the ambulatory system 105, auditor device 170, and the external system 125 as illustrated in FIG. 1. The device audit system 200A may include one or more of an auditor device 210A, an analyzer unit 220, and an ambulatory medical device (AMD) 230. In an example, the device audit system 200A includes only the auditor device 210A and the analyzer unit 220, and the device audit system 200A may be configured to audit various types of AMDs including but not limited to the AMD 230, or to audit an AMD that operates at different modes such a monitor-only mode, or a monitor-plus-therapy mode.

The auditor device 210A may be an ambulatory device associated with the patient, such as the auditor device 170 as illustrated in FIG. 1, or alternatively an immobile device that may be activated to interact with the patient when the patient enters or remains in an ambient environment of the auditor device 210A. The auditor device 210A may be a tethered device with sensing or stimulation electrodes substantially away from, and connected via a lead wire to, a device body. Alternatively, the auditor device 210A may be a leadless device having one or more electrodes positioned on an outer surface of the device body, rather than through an extended connection such as a lead, wire, or tether. Such a leadless auditor device may include anchoring or fixation means for securing the auditor device on a target location, such as an endocardial or epicardial surface of the heart. Examples of the anchoring or fixation means may include one or more pins, staples, threads, screws, helix, or tines, among other fixation structures.

The auditor device 210A may include a sensor circuit 212 and a controller 214, and consistently monitor the AMD 230 independently of the operation of the AMD 230. The sensor circuit 212 may be coupled to one or more sensors to sense a physiological signal from the patient during the operation of the AMD 230. Examples of the physiological signals may include tissue depolarization, electrogram, cardiac or thoracic impedance, blood pressure signal, heart sounds signal, endocardial acceleration signal, blood-oxygen measurements, respiration rate or tidal volume signal, temperature measurement, blood flow signal, or blood chemicals, among other physiological signals. The auditor device 210A may sense the physiological signals and information about operation of the AMD 230 independently of the operation of the AMD 230. The independent sensing may include consistently sensing the physiological signals and sensing the operation of the AMD without intermittent blanking periods while the AMD delivers therapy such as the electrostimulation.

The controller 214 may control the operation of the sensor circuit 212, such as selecting between first and second sub-circuits substantially within the sensor circuit 212. The first sub-circuit may be configured to sense the stimulation pulses while the AMD 230 delivers electrostimulation. The second sub-circuit may be configured to sense a physiological response to the electrostimulation following the cessation of the electrostimulation. The first and second sub-circuits may include respective signal conditioning components such as one or more of amplifiers, filters, or sampling circuits, among others. In an example, the first sub-circuit may include a bandpass filter with a higher center frequency and a sampling circuit with a higher sampling rate than the second sub-circuit, such that the first sub-circuit may reliably detect the timing and intensity of the stimulation pulses. The controller 214 may automatically select between the first and second sub-circuits to accomplish sensing of desired signals. In another example, the controller 214 may control the operation of the sensor circuit 212 by switching between first and second sensing modes at different temporal phases of electrostimulation. Additionally or alternatively, the controller 214 may switch between a first sensing vector between a first pair of electrodes for sensing the electrostimulation, and a second sensing vector between a second pair of electrodes for sensing the physiological signal in response to the electrostimulation. In an example, the first pair of electrodes may be substantially close to each other such as to eliminate some of the patient's physiological electrical activity, while maintain a high sensitivity in sensing the electrostimulation pulses. The first pair of electrodes may be positioned along a spatial line substantially parallel to, or along the orientation of, the stimulation vector (between stimulation electrodes) employed by the AMD 230 for delivering the electrostimulation. In an example, the second pair of electrodes may be spaced far apart and substantially away from the stimulation electrodes coupled to the AMD 230 for delivering the electrostimulation, such as to eliminate the interference of the electrostimulation pulses.

The AMD 230 may include a sensor circuit 232 and a therapy circuit 234. The sensor circuit 232 may sense a physiological signal and generate information about the operation of AMD. In an example, the information about the operation of AMD may include delivery electrostimulation via the AMD 230, and the sensed physiological signals may provide information about the patient's physiological response to the electrostimulation. The physiological signal sensed by the sensor circuit 232 may be of a different type than the physiological signal sensed by the auditor device 210A. For example, while the sensor circuit 232 senses intracardiac electrogram from an atrium or a ventricle such as by using the lead system 108, the sensor circuit 212 may sense one of a surface electrocardiogram (ECG) from body surface, an epicardial electrogram from outer surface of a heart chamber, or a cardiac mechanical signal such as a blood pressure, flow, heart sounds, or endocardial acceleration signal. Alternatively, the sensor circuit 232 may sense the same type of the physiological signal (e.g., an electrogram) as that sensed at the auditor device 210A, but from a different sensing location such as a different heart chamber or different site of the same heart chamber.

The therapy circuit 234 of the AMD 230 may deliver a therapy such as electrostimulation to a target site. The electrostimulation may include stimulation of one of left ventricle, right ventricle, left atrium, or right atrium of the heart, or a vascular structure associated with the heart. Additionally or alternatively, the electrostimulation may include a neural stimulation of a neural target such as fat pads, atrioventricular node, nerve trunk such as the vagus, carotid and aortic nerves, or baroreceptors, among other neural targets.

The analyzer unit 220 may receive the information generated at the auditor device 210A, including the sensed physiological signals and the sensed information about the operation of the AMD 230, to generate a device audit indicator indicating the functionality of, or the effectiveness of therapy delivered by, the AMD 230. The analyzer unit 220 may be implemented as a part of a microprocessor circuit, which may be a dedicated processor such as a digital signal processor, application specific integrated circuit (ASIC), microprocessor, or other type of processor for processing information including physical activity information. Alternatively, the microprocessor circuit may be a general purpose processor that may receive and execute a set of instructions of performing the functions, methods, or techniques described herein.

The analyzer unit 220 may include circuit sets comprising one or more other circuits or sub-circuits that may, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.) including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The analyzer unit 220 may include one or more of an input circuit 222, a processor circuit 224, a programmer circuit 226, and an output circuit 228. The analyzer unit 220 may be an embodiment of the external system 125, or a component thereof such as the external device 120 or the remote device 124. In an example, a portion or the entirety of the analyzer unit 220 may be integrated within the AMD 230.

The input circuit 222 may receive from the auditor device 210A the sensed physiological signal and the information about operation of the AMD 230, such as via the communication link 175. The data communication between the auditor device 210A and the analyzer unit 220 may be real-time transfer, batched transfer, or one-time memory dump. In an example, data communication is established upon the auditor device 210A receiving a request from the analyzer unit 220. The processor circuit 224 may generate a device audit indicator indicating a performance of the AMD based on the information received from the auditor device 210A, such as the sensed physiological signal and the AMD operation information. In an example, the device audit indicator may include a verification of delivery of stimulation to the patient, a verification of the delivered stimulation evoking a positive tissue depolarization and propagation, or an assessment of therapy effectiveness or undesirable side effects, among others. The device audit indicator may alternatively or additionally indicate the integrity of the lead associated with or the sensing circuits within the AMD. Examples of the processor circuit and the device audit indicators are discussed below, such as with reference to FIG. 3.

In some examples, the input circuit 222 may additionally be coupled the AMD 230 to receive the information about operation of the AMD, such as generated by the sensor circuit 232. The processor circuit 224 may generate the device audit indicator further using the information about the operation of AMD 230 generated by the sensor circuit 232. Such information may include, for example, delivery of the electrostimulation and resultant patient responses to the electrostimulation in the perspective of, and reported by, the AMD 230. Such information may not be identical to the electrostimulation and the patient responses to the electrostimulation in the perspective of and sensed by the auditor device 210A. Examples of the device audit indicators using the information as reported by the AMD and the sensing of the operation of the AMD are discussed below, such as with reference to FIG. 3.

The programmer circuit 226 may program the AMD 230, such as via the communication link 115, based on the device audit indicator. Programming of the AMD 230 may include selecting a different physiological sensor or a sensing modality, switching to a different sensing vector, or adjusting one or more sensing parameters used by the sensor circuit 232, such as on/off period, sensing duration, sampling rate, amplification, or filtering. Programming of the AMD 230 may additionally or alternatively include programming a different therapy type, switching to a different stimulation site or a different stimulation vector, or adjusting one or more therapy parameters such as one or more of pulse width, pulse amplitude, frequency, duty cycle, stimulation duration, on/off period, or otherwise adjusting the therapy dosage or energy delivered as used by the therapy circuit 234. In an example, if the device audit indicator indicates insufficient electrostimulation (e.g., a frequency of biventricular pacing falling below a specified percentage threshold), or if the electrostimulation does not elicit desirable hemodynamic response or improvement in cardiac function (e.g., the sensed physiological signal by the senor circuit 212 having an intensity falling below a threshold), then the programmer circuit 226 may adjust one or more therapy parameters corresponding to more aggressive therapy (e.g., higher pulse amplitude or frequency, or longer stimulation duration), or switching to a different stimulation vector that may yield higher therapeutic effects with less side effects.

The output circuit 228 may output the device audit indicator to a user or a process. In an example, at least a portion of the output circuit 228 may be implemented in the external system 125. The output circuit 228 may generate a human-perceptible presentation of the device audit indicator, optionally along with other information such as the physiological signals or the device operation information generated by the AMD 230, the physiological signals or the information about device operation generated by the auditor device 210A, or an automatically generated recommendation of programming the AMD 230 including values of range of values for the parameters as used by AMD 230 to sense the physiological signals or to deliver the therapy to the patient. The output circuit 228 may include a display for displaying the information. The information may be presented in a table, a chart, a diagram, or any other types of textual, tabular, or graphical presentation formats, for displaying to a system user. The presentation of the output information may include audio or other media format to alert the system user of the detected physiological events. The system user, such as a clinician, may program the AMD 230, or otherwise confirm, override, or otherwise modify the automatically recommended device programming based on the device audit indicator or other information output.

The device audit system 200B as illustrated in FIG. 2B, which may be a variant of the device audit system 200A, may include an auditor device 210B and the ambulatory medical device 230. Similar to the auditor device 210A, the auditor device 210B may include the sensor circuit 212 and controller 214. The auditor device 210B may further include at least a portion of the analyzer unit 220. By way of example and not limitation, and as illustrated in FIG. 2B, at least the processor circuit 224 and the output circuit 228, which are included in the analyzer unit 220 of the device audit system 200A, may be incorporated within the auditor device 210B. As such, the auditor device 210B may be configured to perform at least some of the functions of the analyzer unit 220.

The auditor device 210B may be communicatively coupled to the AMD 230 via a communication link 245, such as a wireless communication link. Examples of the wireless communication link may include radiofrequency (RF) signals, inductive coupling, capacitive coupling, optical signals, acoustic signals, conducted communication signals, or any other signals suitable for communication. Through the communication link 245, the AMD 230 may transmit to the auditor device 210B the information about operation of the AMD 230, such as delivery of the electrostimulation and resultant patient responses to the electrostimulation in the perspective of the AMD 230. Such information may not be identical to the electrostimulation and the patient responses to the electrostimulation in the perspective of and sensed by the auditor device 210B. The processor circuit 224 may generate the device audit indicator using the information about the operation of AMD 230 (such as received from the AMD 230), and the information of the sensed physiological signal and the AMD operation information that is generated by the sensor circuit 212. The output circuit 228 may output the device audit indicator, optionally along with other patient information or AMD information, to a user or a process such as for storing in a memory or being communicated to a patient management system such as the external system 125.

Although the discussion of the device audit system 200A herein focuses on one auditor device 210A or 210B, this is meant only by way of example and not limitation. It is within the contemplation of the inventors, and within the scope of this document, that more than one auditor devices may be included to collaboratively audit the AMD 230. The auditor devices may communicate with the analyzer unit 220 and provide their respective perspectives on the functionality, device integrity, or effectiveness of therapy delivery of the AMD 230. The analyzer unit 220 may time-synchronize the data collected by various auditor devices, and determine a device audit indicator for outputting to a user or a process, or for programming the AMD 230. The auditor devices may each be an embodiment of the auditor device 210A or 210B, such that each auditor device may sense from the patient a physiological signal and information about operation of the AMD 230, independently of the operations of the AMD 230 and other auditor devices. In an example, one or more auditor devices may be configured to sense only information about operation of the AMD 230 such as sensed electrostimulation delivery, while one or more other devices may be configured to sense only the physiological signals in response to the electrostimulation. The auditor devices may be of different types, sense different physiological signals, or coupled to sensors positioned at different body locations. For example, a first auditor device may be a wearable patch that may be positioned at body surface and includes accelerometer sensors for sensing a heart sounds signal, and a second auditor device may be a subcutaneously implantable monitor configured to be at least partially implanted under the skin and includes electrodes for sensing subcutaneous ECG. The second auditor device may additionally or alternatively include one or more sensors such as a pulse oximeter, a blood pressure sensor, or an intracardiac endocardial accelerometer sensor, among others.

Figure 3:
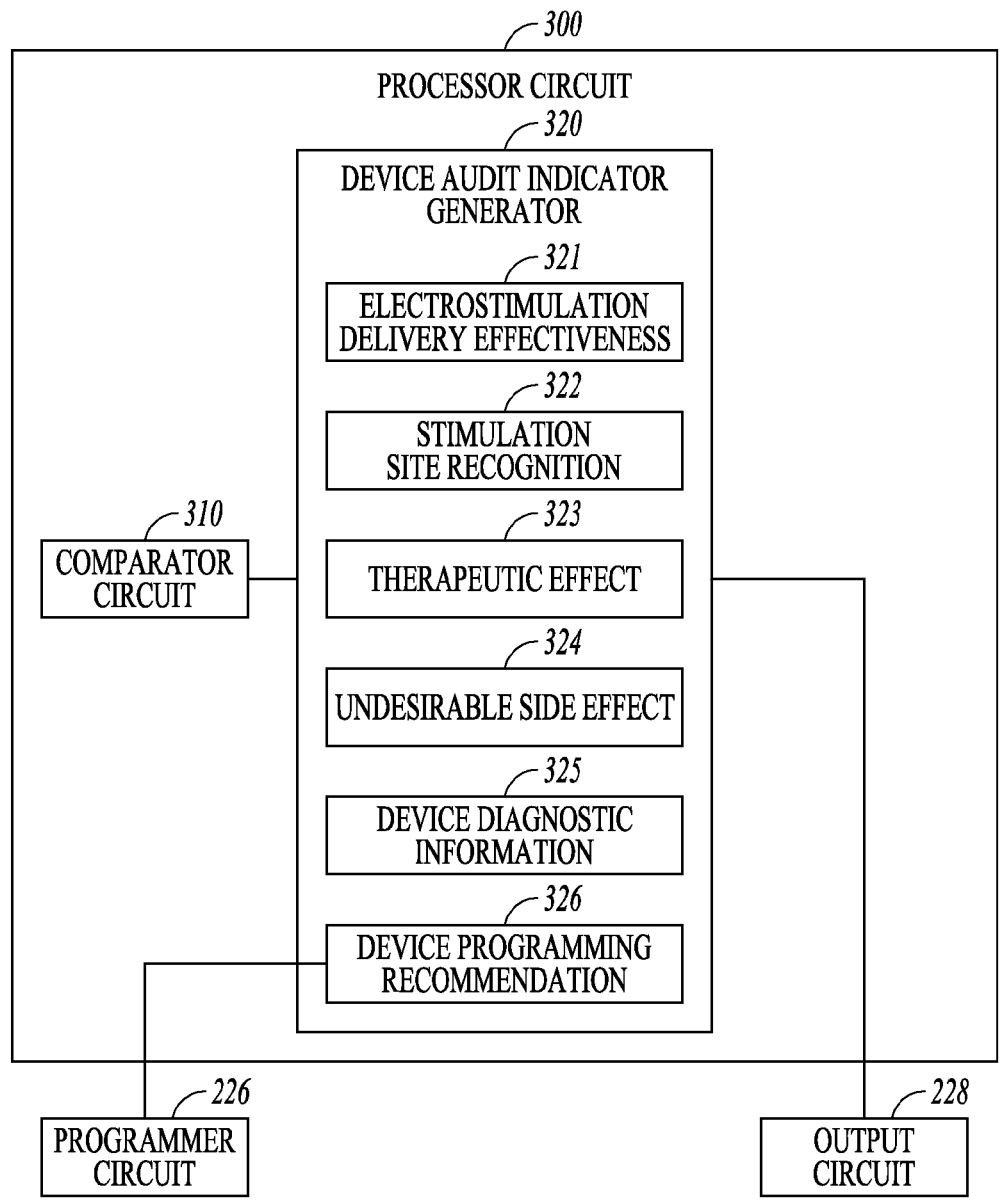
FIG. 3 illustrates generally an example of a processor circuit for auditing operation and functionality of an AMD.

FIG. 3 illustrates generally an example of a processor circuit 300 for auditing operation and functionality of an AMD. The processor circuit 300, which may be an embodiment of the processor circuit 224 in FIG. 2, may include a comparator circuit 310 and auditor indicator generator 320. The comparator circuit 310 may compare the information received from the sensor circuit 212 of the auditor device 210A or 210B and the information received from the AMD 230. In an example, the AMD may include a cardiac device configured to provide cardiac stimulation therapy to one or more chamber of the heart, such as right ventricular (RV) pacing, left ventricular (LV) pacing, or bi-ventricular (BiV) pacing of both left and right ventricles. The comparator circuit 310 may compare the device operation information such as the cardiac pacing pulses generated and reported by the AMD 230, to the device operation information such as the artifacts of the cardiac pacing pulses sensed by sensor circuit 212 of the auditor device 210A or 210B. Discrepancy between the pacing pulses in the perspective of the AMD 230 and the sensed pacing pulses in the perspective of the auditor device may indicate ineffective delivery of the pacing pulses from the AMD to the patient. In another example, the comparator circuit 310 may compare the physiological signals such as an electrical or mechanical response to the cardiac pacing pulses sensed by the AMD 230, to the physiological signals such as an electrical or mechanical response sensed at different locations of the heart or of the body sensed by the sensor circuit 212 of the auditor device 210A or 210B. Discrepancy between the physiological signals sensed by the AMD 230 and the physiological signals sensed by the sensor circuit 212 of the auditor device 210A or 210B may indicate inadequate therapeutic effects or unwanted side effects introduced by the device therapy by the AMD 230.

The device audit indicator generator 320 may be configured to generate one or more device audit indicators indicating the device functionality, integrity, sensing capability, and therapy efficacy associated with the AMD 230. By way of example and not limitation, the device audit indicators may include indicators of electrostimulation delivery effectiveness 321, stimulation site recognition 322, therapeutic effect 323, undesirable side effect 324, device diagnostic information 325, or device programming recommendation 326. In some examples, the device audit indicator generator 320 may generate a composite indictor such as a combination of a plurality of the device audit indicators indicating overall device functionality or therapy efficacy. The auditor indicators may be presented, via the output circuit 228, to a system user such as a clinician, or output to a process such as for storing in a memory or being communicated to a patient management system such as the external system 125.

The electrostimulation delivery effectiveness 321 may indicate how effect the pacing pulses evoke a positive tissue response, such as a cardiac depolarization that propagates through cardiac tissue. A capture occurs when a pacing pulse evokes a positive cardiac tissue response. A non-capture occurs when a pacing pulse fails to evoke a positive cardiac tissue response. A fusion occurs when a pacing pulse is delivered coincidental to a depolarization by an intrinsic cardiac activation. In an example, the electrostimulation delivery effectiveness 321 may be represented by statistics of capture, non-capture, or fusion during a specified period, such as within a day. Examples of the statistics of the electrostimulation delivery may include percentages or distributions of capture beats, non-capture beats, and fusion beats in response to one or more of RV pacing, LV pacing, BiV pacing, RA pacing or other programmed pacing mode. Because the auditor device 210A or 210B consistently senses the AMD 230's delivery of electrostimulation independently of the operation of the AMD 230 (such as without being blanked during the electrostimulation delivery), \ auditor device 210A or 210B may provide a reliable appraisal of the effects of electrostimulation, such as presence and statistics of capture, non-capture, or fusion beats. Other information such as the patient's atrial fibrillation (AF) burden or other tachyarrhythmias and their impact on the effectiveness of electrostimulation delivery may also be determined. The statistics of various capture status may be presented, optionally along with other physiological signals sensed by the AMD 230, or by the auditor device 210A or 210B, to a user via the output circuit 228.

The stimulation site recognition 322 may indicate a device's capability of recognizing site of stimulation, such as being one of a plurality of cardiac sites where the pacing pulses have been delivered. In an example, the auditor device 210A or 210B may consistently detect, independently of the operation of the AMD 230, the pacing pulses delivered by the AMD 230 at various heart chambers, such as atrial pacing (AP) pulses, RV pacing (RVP) pulses, LV pacing (LVP) pulses, or the pacing pulses delivered at different sites of a specified heart chamber, such as pacing at a first LV site (LVaP), or pacing at a second LV site (LVbP), etc. The auditor device 210A or 210B may distinguish pacing at one site from pacing at another site using the temporal information, such as a predetermined sequence of pacing pulses within a cardiac cycle (e.g., AP, followed by RVP, followed by LVaP, which is simultaneous with or followed by LVbP). Recognition of the pacing sites may additionally or alternatively be based on device programming information pertaining to the AMD 230, such as pacing mode, atrioventricular (AV) pacing delay, inter-ventricular (LV-RV) pacing delay, or intraventricular (LVa-LVb) pacing delay, among others. The device programming information may be provided by the system user, transferred from device, or retrieved from a memory or from a programming device such as the external system 125. In some examples, the AMD 230 may employ distinct pacing pulses to pace at various cardiac sites, such as pacing pulses with unique frequency or pulse width, or other site-specific pacing characteristics. The auditor device 210A or 210B may further use such site-specific pacing characteristics to recognize pacing pulses. The pacing markers (e.g., AP, RVP, or LVP representing the delivery of pacing pulses), along with the timing or intervals associated with the pacing pulses, may be communicated to the analyzer unit 220, and time-synchronized with the pacing information detected and reported by the AMD 230. The recognition of stimulation site 322 may be based on the comparison of the pacing information obtained from the auditor device 210A or 210B and the AMD 230, which indicate whether the AMD 230 accurately report the temporal relationship among the pacing sequences at various cardiac stimulation sites.

The therapeutic effect 323 indicates effectiveness of the electrostimulation delivered by the AMD 230 in restoring cardiac dyssynchrony or improving cardiac function. The therapeutic effect 323 may be based on the physiological signals sensed by the auditor device 210A or 210B, which are predictive of patient hemodynamic response to the cardiac electrostimulation. Examples of the hemodynamic signal may include a heart rate, a cardiac or thoracic pressure metric, a LV or RV systolic volume, diastolic volume, or stroke volume metric, a cardiac output metric, cardiac timing intervals such has systolic or diastolic timing interval, LV ejection time, echocardiographic metric such as a ratio of early to late ventricular filling velocities (E/A ratio), or a cardiac or thoracic impedance metric, among others. In an example, a Q-LV interval measured from Q wave of a surface ECG to local intrinsic activation at the LV stimulation site (such as detected as the first dominant peak on the LV electrogram) may be correlated to maximum rate of increase in LV pressure (LV dP/dt max, a clinical index to characterize the contractile ability of the heart), thus indicative of LV contractility. Q-LV interval therefore may be used to assess efficacy of the LV electrostimulation therapy delivered using a specified pacing vector. In another example, intensity of S1 heart sounds (such as S1 amplitude) may be correlated to LV dP/dt max, thus indicative of the LV contractility. In another example, the mechanical delay may include left-ventricular ejection time (LVET), an interval from the opening to the closing of the aortic valve (mechanical systole). The LVET may be correlated to hemodynamic of the LV, and may be measured as an interval between S1 and S2 heart sound within the same cardiac cycle. S1 intensity and LVET therefore can each be used to assess efficacy of the LV electrostimulation therapy delivered using a specified pacing vector. In some examples, the therapeutic effects 323 may include therapeutic effect of the electrostimulation on alleviating a bundle branch block condition in a heart failure patient, such as rate-dependent bundle branch blocks.

The undesirable side effect 324 of the electrostimulation may include unintended effects causes by the therapeutic electrostimulation. Examples of the undesirable side effect may include unwanted phrenic nerve stimulation such as caused by unintended excitation of phrenic nerve during cardiac stimulation, or unwanted laryngeal stimulation such as caused by unintended excitation of laryngeal nerve during vagus nerve stimulation.

The device diagnostic information 325 may include information about device integrity or likely causes of device malfunction. Examples of the device diagnostic information 325 may include lead integrity such as dislodged, fractured, or otherwise failed lead, lead repositioning, or lead perforation, sensing circuitry integrity, or battery status, among others. The device diagnostic information 325 may additionally include factors that may affect electrode-tissue interaction or tissue excitatory properties, and thus cause inferior response to electrostimulation. Examples of such factors may include changes in one or more of physical activity (including intensity, duration, or pattern of physical activity), posture, diet, or medication. The device diagnostic information 325 may be generated based on a comparison of the physiological signals or measurements of a self-diagnostic test detected by the AMD 230, and the physiological signals detected by the auditor device 210A or 210B.

The device programming recommendation 326 may include recommended parameter values for event sensing and therapy for use by the AMD 230. The recommended parameter values may be determined based at least on the physiological signals sensed by the auditor device 210A or 210B in response to the electrostimulation. As previously discussed with reference to FIG. 2, the parameters may include one or more parameters for event sensing, and/or one or more parameters for therapy delivery. In an example, if the device audit indicator indicates insufficient delivery of electrostimulation, or if the electrostimulation does not elicit desirable hemodynamic response or improvement in cardiac function, then the programmer circuit 226 may program the therapy circuit 234 with one or more therapy parameters corresponding to more aggressive therapies, such as electrostimulation with higher intensity or more energy, or switching to a different stimulation vector that may yield improved therapeutic effect with less side effects. If the auditor device 210A or 210B detects a physiological signal indicating inferior response to electrostimulation such as the sensed physiological signal falling below a threshold or outside a specified range, then more aggressive therapy may be recommended. The programmer circuit 226 may program the AMD 230 based on the device programming recommendation 326.

Figure 4:
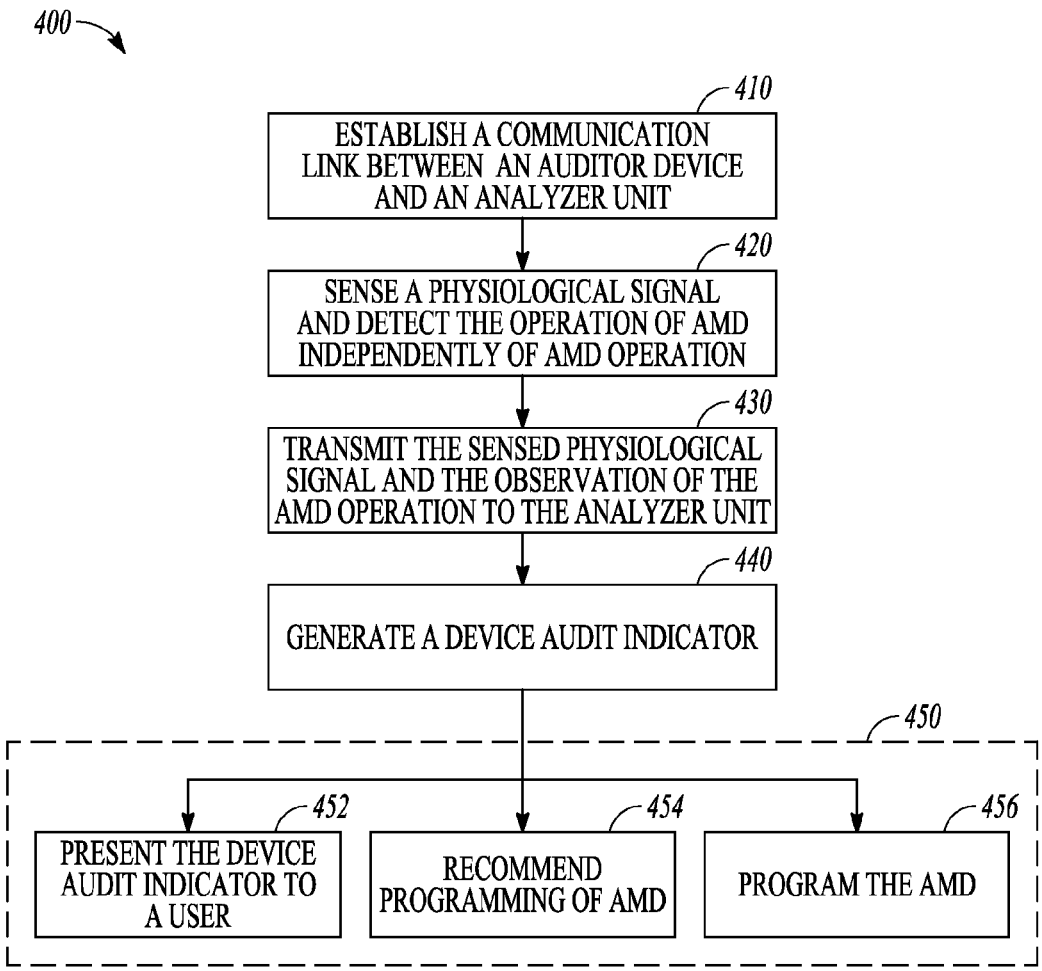
FIG. 4 illustrates generally an example of a method for automatic auditing functionality of or effectiveness of therapy delivery in a medical device.

FIG. 4 illustrates generally an example of a method 400 for automatic auditing functionality or effectiveness of therapy delivery in a medical device, such as the AMD 110 in FIG. 1. The auditing may be performed using an auditor device such as the auditor device 170 associated with the patient, or the auditor device 210A or 210B as illustrated in FIGS. 2A-B. The method 400 may be implemented and operate in the patient management system 100 in FIG. 1 or the device audit system 200A or 220B in FIGS. 2A-B, or any modification of such systems.

The method 400 begins at 410 by establishing a communication link between an auditor device and an analyzer unit, such as the analyzer unit 220 in FIG. 2. The analyzer unit may include a local programmer or a remote patient management system. The communication link may include wired or wireless connections, such as the communication link 175 as illustrated in FIGS. 1 and 2.

At 420, a physiological signal and AMD operation information may be consistently sensed from the patient via the auditor device during the operation of the AMD. The sensing of the physiological signal and the AMD operation information may be independent of the operation of the AMD, such that the sensing may be performed during and after therapy delivery without intermittent blanking periods while the AMD delivers electrostimulation. The sensed physiological signal and the AMD operation information sensed by the auditor device represent the auditor device's perspective of the functionality of the AMD. Examples of the physiological signals may include tissue depolarization, electrogram, cardiac or thoracic impedance, blood pressure signal, heart sounds signal, endocardial acceleration signal, blood-oxygen measurements, respiration rate or tidal volume signal, temperature measurement, blood flow signal, or blood chemicals, among other physiological signals suitable to be sensed by one or more sensors associated with the auditor device 210A or 210B. Example of the sensed AMD operation information may include therapy such as electrostimulation delivered to the patient, measurements of self-diagnostic test, sensing of a physiological signal or a physiological measurement, or a medical diagnostic decision, among others. In an example, the sensing of the electrostimulation delivery and the sensing of the physiological signal (such as responses to the delivered electrostimulation) may be performed at different time, such as via the switch controller 214 in FIG. 2. The electrostimulation delivery may be sensed during the AMD delivering electrostimulation, and the physiological response to electrostimulation may be sensed following the delivery of the electrostimulation.

At 430, the physiological signal and the AMD operation information sensed by the auditor device may be transmitted to the analyzer unit, such as via the communication link 175. The data communication may be real-time transfer, batched transfer, or one-time memory dump, such as upon receiving a request from the analyzer unit.

In some examples, the auditor device may be directly coupled to the analyzer unit, such that the data acquired by the auditor device may become available at the analyzer unit in substantially real time. In such a case, establishment of the communication link at 410 and the data transmission at step 430 may be omitted.

At 440, a device audit indicator may be generated based on the sensed physiological signal and the AMD operation information. The device audit indicator may indicate one or more of device functionality, sensing integrity, and therapy efficacy associated with the AMD. In some examples, the device audit indicator may be generated further using the information about the operation of AMD as detected and reported by the AMD. Such information may include delivery of the electrostimulation and the patient response to the electrostimulation reported by the AMD, which may not be identical to the electrostimulation and the patient responses detected by the auditor device. Such information may be transmitted to an analyzer unit such as the analyzer unit 220 in FIG. 2A, or to the auditor device such as the auditor device 210B in FIG. 2B, where the device audit indicator may be generated. In an example, a comparison between the device operation information produced by the AMD and the device operation information detected by the auditor device may reveal discrepancies between the pacing pulses in the perspective of the AMD and the sensed pacing pulses in the perspective of the auditor device, or discrepancies between the physiological signals sensed by the AMD and the physiological signals sensed by the auditor device. The device audit indicators, such as represented by one or more of such discrepancies, may indicate functional issues pertaining to the AMD such as ineffective delivery of pacing pulses, or inadequate therapeutic effects or unwanted side effects introduced by the electrostimulation as delivered through the AMD.

In an example, the device audit indicator may indicate whether or not electrostimulation, such as cardiac stimulation or neural stimulation at a specified target location, has been delivered. The device audit indicator may include statistics of capture, non-capture, or fusion beats in response to cardiac pacing that occur within a specified period, such as during a day. In another example, the device audit indicator may indicate device's capability of recognizing site of electrostimulation, such as being one of a plurality of cardiac sites where the pacing pulse have been delivered. The recognition of the stimulation site may be based on the timings of the pacing pulses at various cardiac sites within a cardiac cycle, or additionally or alternatively based on pacing mode, atrioventricular pacing delay, inter- or intra-ventricular pacing delay, or site-specific pacing characteristics such as pacing pulses with frequency or pulse width unique to pacing at a particular site, among other program information.

In an example, the device audit indicator may indicate effectiveness of the electrostimulation delivered by the AMD 230 in restoring cardiac dyssynchrony or improving cardiac function, or unintended effects causes by the therapeutic electrostimulation such as phrenic nerve stimulation laryngeal stimulation. In some examples, the device audit indicator may include information about device integrity or likely causes of device malfunction, such as lead integrity such as dislodged, fractured, or otherwise failed lead, lead repositioning, or lead perforation, sensing circuitry integrity, or battery status, among others.

In some examples, a composite indictor may be generated at 440. The composite indicator may be a combination of a plurality of the device audit indicators, which indicates overall device functionality or therapy efficacy. The device audit indicator, or a composite of the indicators, may be used by several processes at 450. For example, at 452 the auditor indicator may be presented to a system user, such as via the output circuit 228. Other information such as the physiological signals or the device operation information generated by the AMD, the physiological signals or the device operation information generated by the auditor device, may optionally be presented along with the auditor indicator.

Additionally or alternatively, at 454 the device audit indicator may be used to automatically generate a recommendation for programming the AMD. The programming of the AMD may include recommended parameter values for sensing the physiological signals or for delivering the therapy to the patient. Examples of the sensing parameters may include a selection of a physiological sensor or a sensing modality, a sensing vector for sensing electrical potentials, on/off period or duration, sampling rate, amplification, or filtering. Examples of the therapy parameters may include delivery mode, stimulation site, stimulation vector, pulse width, pulse amplitude, frequency, duty cycle, stimulation duration, on/off period, or therapy dosage or energy. In an example, if the device audit indicator indicates insufficient amount of cardiac captures elicited by the electrostimulation at one or more cardiac sites, or if the electrostimulation does not produce desirable hemodynamic response or improvement in cardiac function, then therapy parameter corresponding to more aggressive therapy may be programmed into the AMD. The system user, such as a clinician, may confirm, override, or otherwise modify the automatically recommended device programming based on the device audit indicator or other information output.

Additionally or alternatively, at 456 the AMD may be programmed, automatically or with user intervention, based on device audit indicator or according to the recommend programming of the AMD. In an example, the AMD may be programmed to deliver electrostimulation to a cardiac tissue, a nerve tissue, or other target tissues, or to deliver drug therapy to a tissue or an organ. The electrostimulation therapy may include cardiac pacing at one or more cardiac sites to rectify dyssynchrony or to improve cardiac function in patients with advanced heart failure.

In some examples, the method 400 may include using more than one auditor device to collaboratively audit the performance of the AMD. For example, at 410, a plurality of auditor devices may be communicated with the analyzer unit and provide their respective perspectives on the functionality, device integrity, or effectiveness of therapy delivery of the AMD. At 420, the auditor devices may each independently sense a physiological signal and AMD operation information. Alternatively, some devices may produce only information about operation of the AMD 230, such as sensed electrostimulation delivery, while some other auditor devices may be configured to sense only the physiological signal indicating cardiac or hemodynamic responses to the electrostimulation. The auditor devices may be of different types of devices, sense different physiological signals, or coupled to sensors positioned at different body locations. At 430, the data collected by the auditor devices may be time-synchronized, and one or more device audit indicators may be determined and used by various processes at 450.

The above detailed description includes references to the accompanying drawings, which form a part of the detailed description. The drawings show, by way of illustration, specific embodiments in which the disclosure may be practiced. These embodiments are also referred to herein as "examples." Such examples may include elements in addition to those shown or described. However, the present inventors also contemplate examples in which only those elements shown or described are provided. Moreover, the present inventors also contemplate examples using any combination or permutation of those elements shown or described (or one or more aspects thereof), either with respect to a particular example (or one or more aspects thereof), or with respect to other examples (or one or more aspects thereof) shown or described herein.

In the event of inconsistent usages between this document and any documents so incorporated by reference, the usage in this document controls.

In this document, the terms "a" or "an" are used, as is common in patent documents, to include one or more than one, independent of any other instances or usages of "at least one" or "one or more." In this document, the term "or" is used to refer to a nonexclusive or, such that "A or B" includes "A but not B," "B but not A," and "A and B," unless otherwise indicated. In this document, the terms "including" and "in which" are used as the plain-English equivalents of the respective terms "comprising" and "wherein." Also, in the following claims, the terms "including" and "comprising" are open-ended, that is, a system, device, article, composition, formulation, or process that includes elements in addition to those listed after such a term in a claim are still deemed to fall within the scope of that claim. Moreover, in the following claims, the terms "first," "second," and "third," etc. are used merely as labels, and are not intended to impose numerical requirements on their objects.

Method examples described herein may be machine or computer-implemented at least in part. Some examples may include a computer-readable medium or machine-readable medium encoded with instructions operable to configure an electronic device to perform methods as described in the above examples. An implementation of such methods may include code, such as microcode, assembly language code, a higher-level language code, or the like. Such code may include computer readable instructions for performing various methods. The code may form portions of computer program products. Further, in an example, the code may be tangibly stored on one or more volatile, non-transitory, or non-volatile tangible computer-readable media, such as during execution or at other times. Examples of these tangible computer-readable media may include, but are not limited to, hard disks, removable magnetic disks, removable optical disks (e.g., compact disks and digital video disks), magnetic cassettes, memory cards or sticks, random access memories (RAMs), read only memories (ROMs), and the like.

The above description is intended to be illustrative, and not restrictive. For example, the above-described examples (or one or more aspects thereof) may be used in combination with each other. Other embodiments may be used, such as by one of ordinary skill in the art upon reviewing the above description. The Abstract is provided to comply with 37 C.F.R. § 1.72(b), to allow the reader to quickly ascertain the nature of the technical disclosure. It is submitted with the understanding that it will not be used to interpret or limit the scope or meaning of the claims. Also, in the above Detailed Description, various features may be grouped together to streamline the disclosure. This should not be interpreted as intending that an unclaimed disclosed feature is essential to any claim. Rather, inventive subject matter may lie in less than all features of a particular disclosed embodiment. Thus, the following claims are hereby incorporated into the Detailed Description as examples or embodiments, with each claim standing on its own as a separate embodiment, and it is contemplated that such embodiments may be combined with each other in various combinations or permutations. The scope of the disclosure should be determined with reference to the appended claims, along with the full scope of equivalents to which such claims are entitled.

What is claimed is:

1. A system for automatically auditing an operation of an ambulatory medical device (AMD) associated with a patient, the system comprising:
   an auditor device configured to sense from the patient, independently of and during the operation of the AMD, a physiological signal and information about AMD operation; and
   an analyzer unit communicatively coupled to the auditor device, the analyzer unit comprising:
     an input circuit configured to receive from the auditor device the sensed physiological signal and the sensed AMD operation information;
     a processor circuit configured to generate a device audit indicator indicating a performance of the AMD using the sensed physiological signal and the sensed AMD operation information; and
     an output circuit configured to output the device audit indicator to a user or a process.

2. The system of claim 1, further comprising the AMD communicatively coupled to the analyzer unit, wherein:
   the AMD is configured to generate information about the operation of AMD; and
   the analyzer unit is configured to receive the AMD operation information generated by the AMD, and generate the device audit indicator further using the AMD operation information generated by the AMD.

3. The system of claim 2, wherein the analyzer unit further includes a programmer circuit configured to program the AMD based on the device audit indicator.

4. The system of claim 2, wherein:
   the AMD includes a therapy circuit configured to deliver a therapy to the patient; and
   the programmer circuit of the analyzer unit is configured to program the AMD including program a therapy with specified therapy parameters.

5. The system of claim 1, wherein the auditor device includes an ambulatory device associated with the patient, the ambulatory device including one of:
   an ambulatory sensor patch;
   a wearable device;
   a portable external monitor; or
   an implantable or subcutaneous monitor.

6. The system of claim 1, wherein the auditor device includes an immobile device configured to sense the patient physiological signal in an ambient environment of the patient.

7. The system of claim 1, wherein:
   the AMD operation information sensed by the auditor device includes a sensed electrostimulation delivered via the AMD;
   the sensed physiological signal includes a sensed physiological response to the electrostimulation; and
   the device audit indicator indicates an effectiveness of the electrostimulation based on the sensed electrostimulation and the sensed physiological response to the electrostimulation.

8. The system of claim 7, wherein the sensed electrostimulation includes a sensed cardiac stimulation or a sensed neural stimulation delivered from the AMD.

9. The system of claim 7, wherein the analyzer unit is configured to generate the device audit indicator indicating on or more of:

statistics of tissue capture, non-capture, or fusion in response to the electrostimulation;
stimulation site recognition;
a therapeutic effect of the electrostimulation; or
an undesirable side effect of the electrostimulation.

10. The system of claim 1, wherein the analyzer unit is configured to generate the device audit indicator including device diagnostic information about the AMD.

11. The system of claim 1, wherein the analyzer unit is configured to generate the device audit indicator including a recommendation for programming the AMD.

12. The system of claim 1, comprising first and second auditor devices each communicatively coupled to the analyzer unit, wherein:
the first auditor device is configured to sense, independently of and during the operation of the AMD, a first physiological signal and first AMD operation information;
the second auditor device is configured to sense, independently of and during the operation of the AMD, a different second physiological signal and second AMD operation information; and
the analyzer unit is configured to generate the device audit indicator using the first and second sensed physiological signals and the first and second sensed AMD operation information.

13. The system of claim 1, further comprising the AMD communicatively coupled to the auditor device, wherein at least a portion of the analyzer unit is incorporated within the auditor device.

14. A method of operating an auditor device to automatically audit an operation of an ambulatory medical device (AMD) associated with a patient, the method comprising:
sensing from the patient, via the auditor device and independently of and during the operation of the AMD, a physiological signal and information about AMD operation;
generating a device audit indicator indicating a performance of the AMD using the sensed physiological signal and the sensed AMD operation information; and
outputting the device audit indicator to a user or a process.

15. The method of claim 14, further comprising:
establishing a communication link between the auditor device and an analyzer unit; and
transmitting the sensed physiological signal and the sensed AMD operation information to the analyzer unit via the communication link.

16. The method of claim 14, further comprising generating, via the AMD, information about the operation of AMD;
wherein generating the device audit indicator includes further using the information about the operation of AMD generated by the AMD.

17. The method of claim 14, further comprising programming the AMD including programming a therapy based on the device audit indicator.

18. The method of claim 14, wherein:
the AMD operation information sensed by the auditor device includes a sensed electrostimulation delivered via the AMD;
the sensed physiological signal includes a sensed physiological response to the electrostimulation, and
the device audit indicator indicates an effectiveness of the electrostimulation based on the sensed electrostimulation and the sensed physiological response to the electrostimulation.

19. The method of claim 18, wherein the electrostimulation delivered via the AMD includes a cardiac stimulation or a neural stimulation.

20. The method of claim 18, wherein generating the device audit indicator includes generating one or more indicators of:
statistics of tissue capture, non-capture, or fusion in response to the electrostimulation;
stimulation site recognition;
a therapeutic effect of the electrostimulation;
an undesirable side effect of the electrostimulation;
device diagnostic information about the AMD; or
a recommendation for programming the AMD.

* * * * *